(12) United States Patent
Connell et al.

(10) Patent No.: US 12,708,700 B2
(45) Date of Patent: Aug. 18, 2026

(54) ANTI-MICROBIAL ACTIVITY THROUGH A PROTECTIVE COATING ON MEDICAL ARTICLES

(71) Applicant: Solventum Intellectual Properties Company, Maplewood, MN (US)

(72) Inventors: Jodi L. Connell, St. Paul, MN (US); Audrey A. Sherman, Woodbury, MN (US); Daniel J. Rogers, Grant, MN (US); Ranjani V. Parthasarathy, Woodbury, MN (US)

(73) Assignee: Solventum Intellectual Properties Company, Eagan, MN (US)

( * ) Notice: Subject to any disclaimer, the term of this patent is extended or adjusted under 35 U.S.C. 154(b) by 255 days.

(21) Appl. No.: 18/681,681

(22) PCT Filed: Aug. 25, 2022

(86) PCT No.: PCT/IB2022/057975
§ 371 (c)(1),
(2) Date: Feb. 6, 2024

(87) PCT Pub. No.: WO2023/026232
PCT Pub. Date: Mar. 2, 2023

(65) Prior Publication Data

US 2025/0108151 A1 Apr. 3, 2025

Related U.S. Application Data

(60) Provisional application No. 63/237,606, filed on Aug. 27, 2021.

(51) Int. Cl.
*A61L 29/16* (2006.01)
*A61L 29/02* (2006.01)
(Continued)

(52) U.S. Cl.
CPC ............... *A61L 29/16* (2013.01); *A61L 29/02* (2013.01); *A61L 29/041* (2013.01); *A61L 29/06* (2013.01);
(Continued)

(58) Field of Classification Search
None
See application file for complete search history.

(56) References Cited

U.S. PATENT DOCUMENTS

| | | | |
|---|---|---|---|
| 5,067,491 | A | 11/1991 | Taylor, II |
| 7,445,628 | B2 | 11/2008 | Ragheb |

(Continued)

FOREIGN PATENT DOCUMENTS

| | | | |
|---|---|---|---|
| CN | 103132045 | A | 6/2013 |
| EP | 1830712 | A1 | 9/2007 |

(Continued)

OTHER PUBLICATIONS

Optical Clarity of Parylene at Increased Thickness, 2023, Specialty Coating Systems, pp. 4-6 (Year: 2023).*

(Continued)

*Primary Examiner* — Thomas J Kessler

(57) ABSTRACT

Medical articles include a tube prepared from a polymer composition containing one or more extractable components. At least a portion of the exterior surface of the tube contains an anti-microbial layer. A transparent vapor-deposited coating of a barrier polymer derived from at least one ethylenically unsaturated monomer covers the exterior surface of the tube. The barrier coating reduces the extraction of extractable component(s) from the tube, but permits the anti-microbial to pass through the barrier layer and provide anti-microbial activity on the barrier surface.

20 Claims, 3 Drawing Sheets

(51) Int. Cl.
*A61L 29/04* (2006.01)
*A61L 29/06* (2006.01)

(52) U.S. Cl.
CPC ... *A61L 2300/208* (2013.01); *A61L 2300/404* (2013.01); *A61L 2300/608* (2013.01); *A61L 2420/02* (2013.01); *A61L 2420/08* (2013.01)

(56) References Cited

U.S. PATENT DOCUMENTS

| | | | | |
|---|---|---|---|---|
| 2005/0281858 | A1 | 12/2005 | Kloke | |
| 2008/0093157 | A1 * | 4/2008 | Drummond | A61B 7/02 181/131 |
| 2008/0171087 | A1 | 7/2008 | Chappa | |
| 2010/0266794 | A1 * | 10/2010 | Wright | C08F 290/061 264/496 |
| 2013/0045146 | A1 * | 2/2013 | Peters | B01L 3/5635 422/547 |
| 2015/0165097 | A1 * | 6/2015 | Parthasarathy | A61L 31/16 514/340 |
| 2018/0236144 | A1 * | 8/2018 | Caballero | B05D 7/02 |

FOREIGN PATENT DOCUMENTS

| | | | |
|---|---|---|---|
| KR | 20030034119 | A | 5/2003 |
| WO | 9959646 | W | 11/1999 |
| WO | 200622854 | W | 3/2006 |
| WO | 200822258 | W | 2/2008 |
| WO | 200839749 | W | 4/2008 |
| WO | 2012166291 | A2 | 12/2012 |
| WO | 2014008264 | A1 | 1/2014 |
| WO | 2020209828 | A1 | 10/2020 |
| WO | 2021033151 | A1 | 2/2021 |
| WO | 2021033162 | A1 | 2/2021 |
| WO | 2021236429 | A1 | 11/2021 |
| WO | 2022123440 | A1 | 6/2022 |
| WO | 2022162528 | A1 | 8/2022 |

OTHER PUBLICATIONS

Franklin Trevor et al, “Vapor-Deposited Biointerfaces and Bacteria: An Evolving Conversation”, Dec. 16, 2019 (Dec. 16, 2019), vol. {0} 6, No. {0} 1, p. 182-197.

International Search Report for PCT/IB2022/057975, mailed on Dec. 8, 2022, 5 pages.

* cited by examiner

ANTI-MICROBIAL ACTIVITY THROUGH A PROTECTIVE COATING ON MEDICAL ARTICLES

SUMMARY

Disclosed herein are medical articles and methods for preparing medical articles. The medical articles have a barrier coating that covers an anti-microbial layer, and the article displays anti-microbial activity despite the anti-microbial layer being covered by the barrier coating.

In some embodiments, the medical article comprises a tube with an interior surface and an exterior surface, where the tube comprises a polymer composition containing one or more extractable components. At least a portion of the exterior surface of the tube contains an anti-microbial. A transparent vapor-deposited coating of a barrier polymer derived from at least one ethylenically unsaturated monomer covers at least a portion of at least the exterior surface of the tube, such that the vapor-deposited polymer coating barrier reduces the extraction of extractable component(s) from the tube, and at least a portion of the anti-microbial is capable of passing through the barrier polymer layer providing anti-microbial activity on the surface of the barrier polymer surface.

Also disclosed are methods of preparing medical articles. In some embodiments, the method comprises providing a tube with an interior surface and an exterior surface, where the tube comprises a polymer composition containing one or more extractable components, disposing an anti-microbial on at least a portion of the exterior surface of the tube, and vapor coating a barrier polymer derived from at least one ethylenically unsaturated monomer onto at least a portion of at least the exterior surface of the tube.

BRIEF DESCRIPTION OF THE DRAWINGS

The present application may be more completely understood in consideration of the following detailed description of various embodiments of the disclosure in connection with the accompanying drawings.

Figure 1:
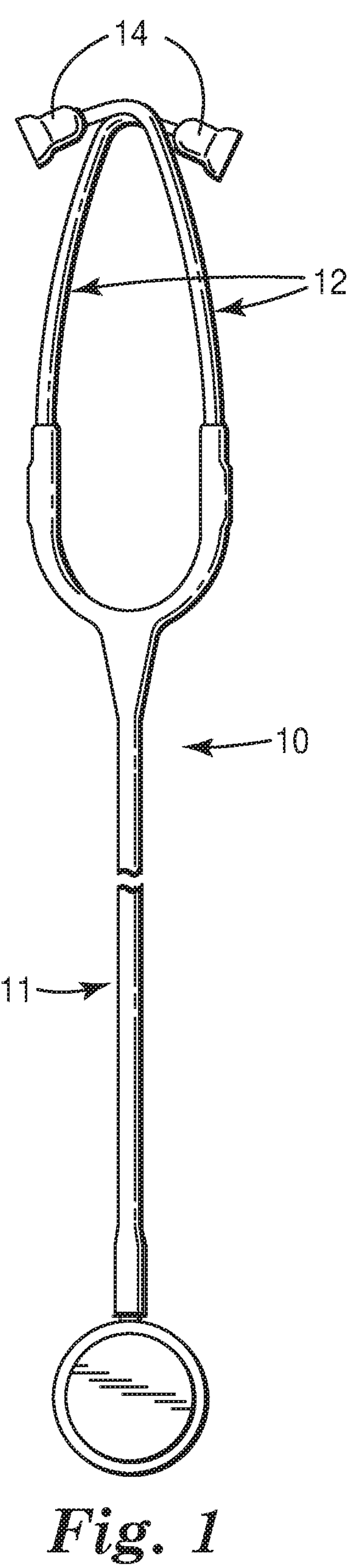
FIG. 1 is a top view of a stethoscope incorporating a tubing article of this disclosure.

In the following description of the illustrated embodiments, reference is made to the accompanying drawings, in which is shown by way of illustration, various embodiments in which the disclosure may be practiced. It is to be understood that the embodiments may be utilized and structural changes may be made without departing from the scope of the present disclosure. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Medical articles, since they are used in medical environments, are exposed to a wide range of environments, such as microbe-rich environments. This exposure can permit the medical articles to form a conduit for the spreading of microbes. A wide range of anti-microbial materials have been developed to treat surfaces to mitigate the transfer of microbes. There are a number of issues with the treatment of medical article surfaces with anti-microbial materials. In some instances, the use of anti-microbial materials on the surface of a medical article changes the properties of that medical article. For example, many anti-microbial materials give the surface of the medical article a greasy or oily feel which can be undesirable. In other instances, the anti-microbial material can change the appearance of the surface of the article or can change the physical properties of the medical article. Particularly challenging in this regard are articles that are flexible, as described below. Also, some anti-microbial materials are irritating to the skin, and thus are undesirable in articles that come into contact with skin.

A wide range of medical devices and articles are prepared from polymeric materials. Many of these articles and devices desirably have flexibility. Beside the anti-microbial issues described above, flexible materials have additional complicating issues. Among the flexible materials used are polymers that contain extractable materials such as plasticizers, fillers, tackifiers, heat stabilizers, and the like. These extractable materials are often present in large quantities. The extractable materials can be extracted from the polymer by exposure to solvents, by heat, by contact with fluids such as aqueous or hydroalcoholic disinfectants, by high humidity (e.g. >90% relative humidity), by contact with skin, or even over time. This extraction is undesirable for many reasons and can cause difficulties in the use of the medical articles.

One particularly useful polymeric material is polyvinyl chloride (PVC) often referred to as "vinyl". PVC by itself is a rigid material, and thus plasticizers are added to the material to make it softer and more flexible. Among the commonly used plasticizers are phthalates. In recent years, the use of phthalate plasticizers in PVC for medical uses has fallen into disfavor, and phthalate-free PVC materials are being used more and more in medical applications. However, as is well known in the chemical arts, making a change in composition often causes changes in the properties of the materials.

PVC materials are frequently used in tubing materials, such as the sound transmitting tubes of stethoscopes. These tubes have a variety of required property features. Among these properties are flexibility, resistance to degradation from exposure to heat and chemicals, durability, an aesthetically pleasant look, and a pleasant feel. The introduction of phthalate-free PVC materials has been observed to adversely affect some or all of these properties. As the stethoscopes are used, washing, and exposure to the body heat of the user tends to cause the PVC material to become more rigid as plasticizer leaches out or is washed away.

In addition to the requirements for flexibility, durability, and aesthetics, it is desirable to add the feature of anti-microbial activity. As was mentioned above, the addition of an anti-microbial to the surface of the flexible medical article can change the aesthetic or physical properties of the article. Therefore, there is a need for flexible articles that prevent the leaching of plasticizer from the flexible material and also have anti-microbial activity.

In this disclosure, it has been found that depositing a barrier coating onto polymeric tubes that contain extractable components and have an anti-microbial on the surface gives desirable properties. The barrier coating is a vapor-deposited coating of a polymer derived from at least one ethylenically unsaturated monomer. The barrier coating not only reduces the extractability of the extractable components form the polymeric tube, but also provides an article with anti-microbial activity. In addition, the coating provides a variety of additional desirable features. Among these features are optical transparency and tactile features such as a desirable texture, and coefficient of friction. Because the coating protects the tubing, the tubing retains its desirable properties over the lifetime of the article.

Disclosed herein are tubes useful in tubing articles, where the tubes comprise a polymer composition containing one or more extractable components with an anti-microbial on at least a portion of one surface of the tube, where the tube article has a vapor-deposited coating of a barrier polymer derived from at least one ethylenically unsaturated monomer on at least the exterior surface of the tube. In some embodiments, the vapor-deposited coating is present on both the interior and exterior surface of the tube. The barrier polymer is derived from at least one ethylenically unsaturated monomer and may be optionally crosslinked by incorporation of at least one dimeric ethylenically unsaturated monomer. The vapor-deposited barrier polymer coating reduces the extraction of extractable component(s) from the tube without blocking the anti-microbial activity of the anti-microbial agent present on the tube. Additionally, the protective coating provides a cleanable surface. By this it is meant that if the surface becomes soiled or marked, the soiling or marking can be removed without removing or adversely affecting the coating. In this way, the protective coating not only protects the article surface and permits the cleaning of the article surface, but also reduces the extraction of extractable components from the tube and provides anti-microbial activity. Also disclosed are methods of preparing tubing articles, such as medical articles. Among the tubing articles are stethoscopes.

The term "tube" and "tubing" as used herein refers to a three-dimensional tubular article that is cylindrically symmetric. Tubes and tubing are defined by an inner diameter, an outer diameter, (the thickness of the tubing is the difference between the outer diameter and the inner diameter) and a length. While the thickness of the tubing can vary slightly through the length of the tube as the result of the method of preparation, etc., no intentional asymmetries are present in the tubing. Typically, the length is substantially greater than the diameter of the tube.

The term "microorganism" is generally used to refer to any prokaryotic or eukaryotic microscopic organism, including without limitation, one or more of bacteria (e.g., motile or nonmotile, vegetative or dormant, Gram positive or Gram negative, planktonic or living in a biofilm), bacterial spores or endospores, algae, fungi (e.g., yeast, filamentous fungi, fungal spores), mycoplasmas, and protozoa, as well as combinations thereof. In some cases, the microorganisms of particular interest are those that are pathogenic, and the term "pathogen" is used to refer to any pathogenic microorganism. Examples of pathogens can include, but are not limited to, both Gram positive and Gram negative bacteria, fungi, and viruses including members of the family Enterobacteriaceae, or members of the family Micrococaceae, or the genera *Staphylococcus* spp., *Streptococcus*, spp., *Pseudomonas* spp., *Acinetobacter* spp., *Enterococcus* spp., *Salmonella* spp., *Legionella* spp., *Shigella* spp., *Yersinia* spp., *Enterobacter* spp., *Escherichia* spp., *Bacillus* spp., *Listeria* spp., *Campylobacter* spp., *Acinetobacter* spp., *Vibrio* spp., *Clostridium* spp., *Klebsiella* spp., *Proteus* spp. *Aspergillus* spp., *Candida* spp., and *Corynebacterium* spp. Particular examples of pathogens can include, but are not limited to, *Escherichia coli* including enterohemorrhagic *E. coli* e.g., serotype O157:H7, O129:H11; *Pseudomonas aeruginosa; Bacillus cereus; Bacillus anthracis; Salmonella enteritidis; Salmonella enterica* serotype *Typhimurium; Listeria monocytogenes; Clostridium botulinum; Clostridium perfringens; Staphylococcus aureus*; methicillin-resistant *Staphylococcus aureus*; carbapenem-resistant Enterobacteriaceae, *Campylobacter jejuni; Yersinia enterocolitica; Vibrio vulnificus; Clostridium difficile*; vancomycin-resistant *Enterococcus; Klebsiella pnuemoniae; Proteus mirabilus* and *Enterobacter* [*Cronobacter*] *sakazakii.*

The term "(meth)acrylate" refers to monomeric acrylic or methacrylic esters of alcohols. Acrylate and methacrylate monomers or oligomers are referred to collectively herein as "(meth)acrylates". Materials referred to as "(meth)acrylate functional" are materials that contain one or more (meth) acrylate groups.

The terms "polysiloxane" and "siloxane-based" as used herein refer to polymers or units of polymers that contain siloxane units. The terms silicone or siloxane are used interchangeably and refer to units with dialkyl or diaryl siloxane ($—SiR_2O—$) repeating units.

The terms "room temperature" and "ambient temperature" are used interchangeably to mean temperatures in the range of 20° C. to 25° C.

Unless otherwise indicated, the terms "optically transparent", and "visible light transmissive" are used interchangeably, and refer to a layer, article, or film that has a high light transmittance over at least a portion of the visible light spectrum (about 400 to about 700 nm). Typically, optically transparent articles have a visible light transmittance of at least 90% and a haze of less than 10%.

The terms "polymer" and "macromolecule" are used herein consistent with their common usage in chemistry. Polymers and macromolecules are composed of many repeated subunits. As used herein, the term "macromolecule" is used to describe a group attached to a monomer that has multiple repeating units. The term "polymer" is used to describe the resultant material formed from a polymerization reaction.

The term "anti-microbial" is used herein according to the commonly used meaning, that is an agent that kills or stops the growth of microorganisms. The terms "anti-microbial" and "anti-microbial gent" are used interchangeably.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The terms "free radically polymerizable" and "ethylenically unsaturated" are used interchangeably and refer to a reactive group which contains a carbon-carbon double bond which is able to be polymerized via a free radical polymerization mechanism.

As used herein the term "PVC" is used as a shorthand definition of polyvinyl chloride. The term "phthalate-free PVC" as used herein refers to a PVC material that does not contain phthalate plasticizer.

As used herein the term "plasticizer" refers to a compound(s) which when added to a polymer results in increased flexibility.

As used herein the term "parylene" is a trade name for a variety of chemical vapor-deposited poly(p-xylylene) polymers. The term is used herein as a generic name for members of a unique polymer series. The basic member of the series, called Parylene N, is poly-para-xylylene, a completely linear, highly crystalline material.

Parylene C, the second commercially available member of the series, is produced from the same monomer modified by the substitution of a chlorine atom for one of the aromatic hydrogens. The structures are shown below.

Parylene D, the third member of the series, is produced from the same monomer modified by the substitution of the chlorine atom for two of the aromatic hydrogens. Parylene D is similar in properties to Parylene C with the added ability to withstand higher use temperatures.

The parylene also may have one or more hydrogen atoms replaced by fluorine. For example, Parylene AF-4 and parylene VT-4 (generic name, per-fluorinated aromatic ring) also known as PARYLENE HT from SCS.

Parylene X is a crosslinkable parylene. Poly(methyl-p-xylylene) or parylene M

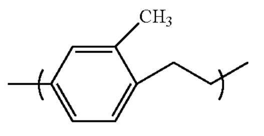

and Parylene E

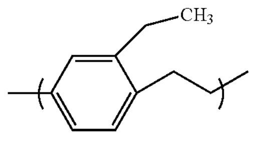

are solvent soluble polymers.

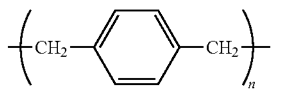

Parlyene N

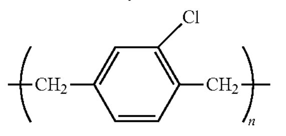

Parlyene C

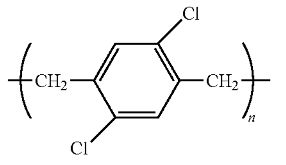

Parlyene D

-continued

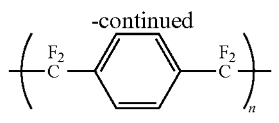

PARYLENE AF-4
or PARYLENE HT

As used herein "parylene copolymers" are chemical vapor-deposited derived from p-xylylene and at least one additional ethylenically unsaturated monomer.

As used herein "parylene coatings" refer to coatings of parylene materials.

Disclosed herein are tubes useful to prepare tubing articles, especially medical articles. The tubes have an interior surface and an exterior surface and are prepared from a polymer composition containing one or more extractable components. The tubes contain an anti-microbial on at least a portion of the exterior surface. The tubes further have a vapor-deposited coating of a barrier polymer derived from at least one ethylenically unsaturated monomer covering at least the exterior surface of the tube and the anti-microbial contained on the exterior surface of the tube. The vapor-deposited barrier polymer coating reduces the extraction of extractable component(s) from the tube. However, at least a portion of the anti-microbial is capable of passing through the barrier polymer layer providing anti-microbial activity on the surface of the barrier polymer surface.

A wide range of polymer compositions containing one or more extractable components are suitable for preparing tubes. In some embodiments, the polymer compositions comprise plasticized polyvinyl chloride (PVC), plasticized PVC copolymers, plasticized polyurethane, or polysiloxanes. Polysiloxanes may or may not include plasticizers like the other classes of polymers, but even if plasticizers are not used in the polysiloxanes, they may contain a variety of extractable materials such as unreacted cyclic siloxane, catalyst residue, tackifier, or a combination thereof. Additionally, any of the above polymer compositions may contain additional materials that may be extractable including stabilizing agents such as thermal stabilizers and UV stabilizers, fillers, and the like.

Polyurethane polymers are well known in the polymer arts, being prepared from the reaction of poly-isocyanates and polyols. A wide range of polyurethane polymers are suitable, including aromatic, aliphatic, urethane block copolymers and copolymers and mixtures thereof. A wide range of plasticizers can be used to plasticize the polyurethane polymers. The polyurethanes may be linear or crosslinked. The polyols used to prepare the polyurethanes may be poly-ether polyols, polyester polyols, aliphatic polyols, siloxane polyols, and the like. The crosslinked polyurethanes are generally made via a 2-part reaction.

Polysiloxane polymers are also well known in the art. Typically, siloxane-based polymers can be prepared in a variety of ways including moisture-curing, hydrosilylation, and condensation reactions. Additionally, a wide range of polysiloxane polymers and polysiloxane precursors are commercially available. As mentioned above, the polysiloxanes can contain a variety of extractable components. Additionally, it can be desirable to apply a barrier coating to polysiloxane tubes, not only as a barrier against leaching of extractable components but also to alter the surface properties of the polysiloxane tube. Polysiloxanes often have a tacky or sticky feel that can be undesirable. Additionally, while efforts are typically expended to ensure that no residual siloxane monomer is present in the polymer that is formed into a tube, these tasks can be labor intensive or expensive and can be avoided through the use of a barrier layer that inhibits or prevents the leaching of extractable material from the polymeric tube.

In many embodiments, the polymer compositions comprise plasticized PVC polymers and plasticized PVC copolymers. PVC copolymers are prepared by copolymerizing one or more ethylenically unsaturated co-monomers with vinyl chloride. An example of a PVC copolymer is polyvinyl chloride-vinyl acetate. Like the PVC polymers described below, the PVC copolymers typically contain plasticizers, often relatively high loadings of plasticizer.

One particularly suitable class of polymers for tubing articles, especially medical tubing articles are PVC polymers. PVC polymers tend to be rigid materials, and therefore plasticizers are added to make the polymers flexible. Typically, the PVC polymer compositions contain a large quantity of plasticizer. The PVC polymer compositions typically contain up to 50-60% by weight plasticizer based on the total weight of the tube composition. In some embodiments, the PVC polymer composition comprises at least 20% by weight plasticizer, typically at least 30% by weight plasticizer, more typically at least 35% by weight plasticizer, or even at least 40% or 45% by weight plasticizer by weight. Generally, the PVC polymer compositions comprise less than 60% by weight plasticizer or less than 55% by weight plasticizer.

As was mentioned above, the use of phthalate-free plasticizers is becoming more prevalent in the preparation of medical articles such as tubing articles. In some embodiments, the polymer composition of the tubes of this disclosure comprise PVC polymer compositions that are free of phthalate plasticizers.

Among the suitable classes of plasticizers are oligomeric or polymeric plasticizers having an average molecular weight of greater than 1000 Daltons, greater than 1500 Daltons, or even greater than 2000 Daltons as determined by GPC with the appropriate standards. Particularly suitable oligomeric or polymeric plasticizers are aliphatic or aromatic polyesters and are available from Hallstar under the PLASTHALL tradename or from Lanxess under the ULTRAMOL brandname.

Another suitable class of plasticizers are sulfonate esters such as MESAMOLL which is an alkylsulphonic acid ester with phenol.

Additional plasticizers include trimellitates such as trimethyl trimellitate, tri-(2-ethylhexyl) trimellitate, tri-(heptyl, nonyl) trimellitate and the like.

Aliphatic dicarboxylic acid-based plasticizers such as bis(2-ethylhexyl)adipate dimethyl adipate, dioctyl adipate, dibutyl sebacate, dibutyl maleate and the like.

Other plasticizers include azelates, benzoates, terephthalates such as dioctyl terephthalate/DEHT (Eastman Chemical Company Trademark: EASTMAN 168), 1,2-Cyclohexane dicarboxylic acid diisononyl ester (BASF trademark: HEXAMOLL DINCH).

Sulfonamides such as N-ethyl toluene sulfonamide (o/p ETSA), ortho and para isomers, glycols and polyethers such as triethylene glycol dihexanoate and tetraethylene glycol diheptanoate.

The polymeric tubes of this disclosure may have a wide range of diameters and thicknesses. Typically, the tubes are not wide tubes, often having an inner diameter of from 1 to 10 millimeters. In some embodiments, the tube has a thickness of from 0.1-7 millimeters. Generally, the tubes are at least 20 centimeters in length, more typically at least 40 centimeters in length.

At least a portion of the surface of the tubing articles comprises an anti-microbial. Anti-microbials are well known in the art as agents that kill or stop the growth of microorganisms. As mentioned above, the addition of an anti-microbial to a surface can adversely affect the aesthetic or physical properties of the surface. This is particularly important with flexible articles like tubing articles. Additionally, the presence of anti-microbials on the surface of the tubing article can adversely affect the feel of the article. In some instances, the anti-microbial can give the article a greasy or oily feel that is undesirable. Also, some anti-microbials are irritating to the skin, and therefore the presence of such anti-microbials on the surface of articles is undesirable.

A wide range of anti-microbials are suitable for use in the articles of this disclosure. In some embodiments, the anti-microbial comprises benzalkonium chloride, copper, silver, quaternary ammonium compounds, polyhexamethylene biguanide, chlorhexidine gluconate, fatty acid monoesters. Benzalkonium chloride is a particularly suitable anti-microbial.

The anti-microbial can be contacted to the surface of the tubing article in a wide variety of ways. In some embodiments, the anti-microbial is contacted to the surface of the tube by soaking, dipping, wiping, coating, printing, or spraying. In some embodiments, the anti-microbial is contacted to the tubing article surface without the anti-microbial being dispersed or dissolved in a liquid medium. In other embodiments, the anti-microbial is contacted to the tubing article surface as a solution or dispersion, and after contacting the anti-microbial to the tubing article surface that tubing article can be allowed to dry. In some embodiments, disposing an anti-microbial on at least a portion of the exterior surface of the tube comprises soaking the tube in a solution of an anti-microbial in a solvent. A wide range of solvents are suitable depending upon the anti-microbial agent used. In some embodiments water and aqueous solvents are suitable, in other embodiments alcohols such as methanol, ethanol and isopropanol are suitable as well ketones such as acetone and MEK (methyl ethyl ketone).

In addition to the anti-microbial, the surface of the tubing article can have additional coatings or surface treatments. In some embodiments, the tubing articles further comprise a discontinuous or continuous layer on the exterior surface of the tube, where the discontinuous or continuous layer comprises a graphic layer such as a printed layer. The printed surface may be a continuous layer so that the printing covers the entire surface, or the printing may be in the form of a pattern. Typically, the printed surface comprises a printed pattern. A wide range of printed patterns can be used including printed designs, indicia, geometric patterns, and the like. Examples of suitable graphic layers that can be printed onto the article surface include such things as the patterns of UPC or QR codes, decorative patterns such as art and logos, and the like. While the application of layers can be generally be done in any order, typically, the graphic layer, if present, is disposed on the tubing article surface prior to the application of the anti-microbial.

A wide range of printing techniques can be used to form the printed surface. In some embodiments, the printing can be carried out using conventional printing techniques such as screen printing and inkjet printing as well as a variety of contact printing techniques such as flexographic printing, patterned roll coating, letterpress printing, lithography, stencil printing, and the like. Because the tubes are three-dimensional articles, printing using the above conventional printing techniques can be difficult. One particularly suitable technique is hydrographic printing.

Hydrographic printing, also known as water transfer printing and immersion printing, is a method of applying printed designs to three-dimensional surfaces. In the process, a polyvinyl alcohol hydrographic film, which has been gravure-printed with the graphic image to be transferred, is carefully placed on the water's surface in a dipping tank. The clear film is water-soluble, and dissolves after applying an activator solution. Once dipping is begun, the surface tension of the water will allow the pattern to curve around any shape. Any remaining residue is then rinsed off thoroughly. The ink adheres to the desired surface and it cannot be washed off easily. It is then allowed to dry.

To the surface of the article, at least one ethylenically unsaturated monomer is vapor-deposited to form a polymer layer. The vapor-deposited polymer layer is an optically transparent barrier layer. Typically, the polymer barrier layer comprises parylene or a copolymer of parylene. Parylene is the trade name for vapor-deposited poly-para-xylylene. Poly para-xylylene, also referred to as parylene N, is shown in Formula 1 below:

Formula 1

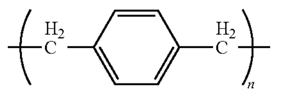

Parylene is prepared when the precursor [2,2]paracyclophane (shown in Formula 2 below) is heated above 550° C. in vacuum. Upon condensation on a surface, the poly-para-xylylene forms.

Formula 2

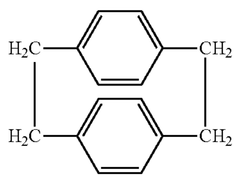

In some embodiments, the vapor-deposited coating of a crosslinked vinyl polymer comprises parylene, that is to say parylene N. In other embodiments, the vapor-deposited coating of a crosslinked vinyl polymer comprises a substituted parylene such as parylene C. Parylene C has the general structure shown in Formula 3 below. Parylene C is prepared by using a chlorine-substituted dimer.

Formula 3

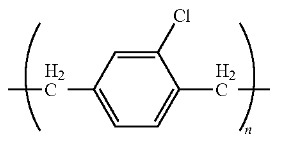

In some embodiments, the vapor-deposited coating of a barrier polymer comprises a copolymer of parylene and at least one (meth)acrylate. A wide variety of (meth)acrylates are suitable. In some embodiments, the (meth)acrylate comprises at least one $C_3$-$C_{18}$ alkyl (meth)acrylate.

The vapor-deposited coating of a barrier polymer can have a wide range of thicknesses. As mentioned above, the coating may be a continuous coating, present on the entire exterior surface of the tubing or it can be present in selective regions of the exterior surface of the tubing. Additionally, the coating may be present on both the interior and exterior surfaces of the tubing. In some embodiments, the vapor-deposited barrier polymer coating has a thickness of from 0.2-10 micrometers. In other embodiments, the vapor-deposited crosslinked vinyl polymer coating has a thickness of from 1-5 micrometers. The coating may have a uniform or essentially uniform thickness, or the coating thickness may vary over the surface of the tubing. Typically, the coating has an essentially uniform thickness.

The vapor-deposited coating of a barrier polymer may comprise additional additives. Among the additives are heat stabilizers, coloring agents, and mold release agents.

One necessary feature of the barrier polymers is their ability to strongly adhere to the tube. This is complicated by the fact that typically the tubing polymeric compositions contain high levels of plasticizer. Among the circumstances that make strong adhesion necessary is in bending. It is desirable that the barrier polymers are able to withstand 1800 bending of the tubing for at least 5,000 cycles, more desirably at least 10,000 cycles and even more desirably at least 20,000 cycles when tested according to a "Bend Test" as is understood in the art.

The vapor-deposited coatings of a barrier polymer of the current disclosure reduce the extractability of the extractable components of the polymer compositions of the tubing and also protect the anti-microbial, and yet the barrier polymer permits the anti-microbial to provide anti-microbial activity. In some embodiments, the coatings prevent the extraction of extractable components from the polymer compositions of the tubing. This extraction refers to a variety of extraction methods. It is particularly desirable that the barrier polymers prevent extraction by both polar fluids such as aqueous and hydroalcoholic (e.g. rubbing alcohol, 70/30 v/v isopropanol water) disinfectants as well as nonpolar fluids such as skin oil (sebum) and synthetic sebum. Examples of extraction methods include solvent extraction, heat extraction, and skin contact extraction. Solvent extraction involves the application of solvent to the polymer composition surface. Suitable solvents are described above and include polar fluids and nonpolar fluids. Upon removal of the solvent by wiping or similar techniques results in extractable components leaving the polymer composition. Heat extraction involves applying heat to the polymer composition which results in the extractable components leaching from the polymer composition. Heat can be used alone or in combination with the solvent extraction method described above. Skin contact extraction results from the contact of skin to the polymer composition where the extractable components in the polymer composition leach from the polymer composition. In practice, medical devices containing tubing articles can encounter each of these extraction methods, or a combination of them. The tubing article may be washed or cleaned with a solvent or other liquid, or the tubing may come into contact with a variety of fluids. Heat extraction can occur from contact with, for example, body heat, or higher temperatures such as, for example 50° C. if the article is left in a vehicle on a hot day. Similarly, skin contact extraction can occur from exposure of the tubing article to skin.

The extractability of extractable components from a polymer composition can be modeled in a variety of ways as is well understood in the art.

Besides the reduction of extractability of the extractable components of the polymer composition of the tubing, in some embodiments, the vapor-deposited coating changes the texture, the coefficient of friction, or a combination thereof. This can be particularly true of polysiloxane tubes which, as described above, can have a tacky or sticky feel.

The coated tubing of the current disclosure can be used to prepare a wide variety of medical articles. One particularly suitable use is for the tubing of stethoscopes. A typical stethoscope is shown in FIG. 1. FIG. 1 shows a top view of stethoscope 10. Stethoscope 10 has tubing 11 attached to dual sound transmitting tubes 12, terminating in ear tips 14. The elements of stethoscope 10 can vary from those shown, but the fundamental elements are present. This disclosure relates to tubing 11. The reduction of extractability of plasticizer desirable features of the tubing 11. Among these features are flexibility, handleability, and pleasing aesthetics. In many cases tubing 11 is prepared from plasticizer-filled PVC polymer. Flexibility is imparted to the PVC polymer by high levels of plasticizer, and retention of this plasticizer within the polymer matrix, in other words the lack of plasticizer extraction, is important to the usefulness of the tubing. Because the PVC polymer, or other polymeric material if used, often have high levels of plasticizer or other extractable components, migration of the plasticizer out of the polymer can occur over time, or the plasticizer can be extracted by washing or cleaning, or by contact with skin either when worn or when handled. Loss of flexibility of the tubing reduces the usefulness of the stethoscope. Handleability relates to the feel of the tubing, which is going to be worn and handled by the user of the stethoscope. Another important feature of handleability also relates to the lack of plasticizer extraction in that if plasticizer exudes from the tubing, the feel of the tubing becomes unpleasant, and plasticizer can be transferred to the user's hand. A variety of aesthetic features including printed patterns, color, texture, gloss, and feel are desirable for the tubing of the stethoscope. Because the tubing comes into frequent contact with skin, the texture and feel of the tubing should be aesthetically pleasant, meaning that the tubing should be smooth and have a low coefficient of friction.

Figure 2:
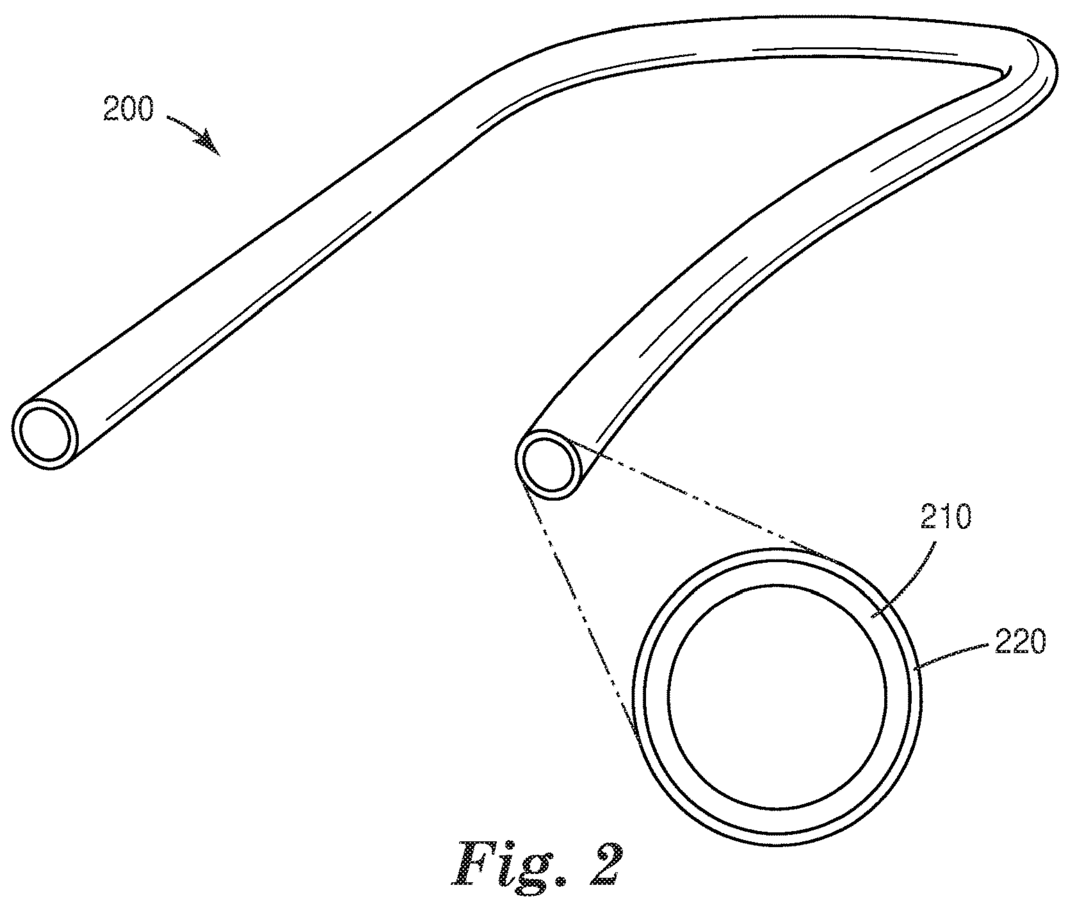
FIG. 2 is a top view of coated tubing of this disclosure, including a cross sectional view of a segment of the coated tubing.

FIG. 2 shows a cross-sectional view of a tubing article of this disclosure. Tubing article 200 has tubing layer 210 with anti-microbial layer 215 and transparent coating layer 220. Anti-microbial layer 215 may be continuous or discontinuous. Transparent coating layer 220 is a vapor-coated barrier layer.

The seemingly paradoxical performance of the vapor-deposited coating on the surface of the tubing articles is quite unexpected. The coating prevents the extraction of plasticizers from the polymeric material of the tubing article while at the same time permitting anti-microbial activity through the coating. While not wishing to be bound by theory, it is believed that the anti-microbial activity may result from anti-microbial passing through or becoming exposed to the outside environment through microcracks in the vapor-deposited coating. In this way, microbes present on the surface of the vapor-deposited coating may contact the anti-microbial either by the anti-microbial passing through the microcracks to bloom to the vapor-deposited coating surface, or the microbes can pass through the microcracks to encounter the anti-microbial. As was mentioned above, some anti-microbial agents are skin irritants, and the vapor-deposited coating provides a barrier to prevent skin irritation when the skin contacts the coated surface of the article.

Figure 3:
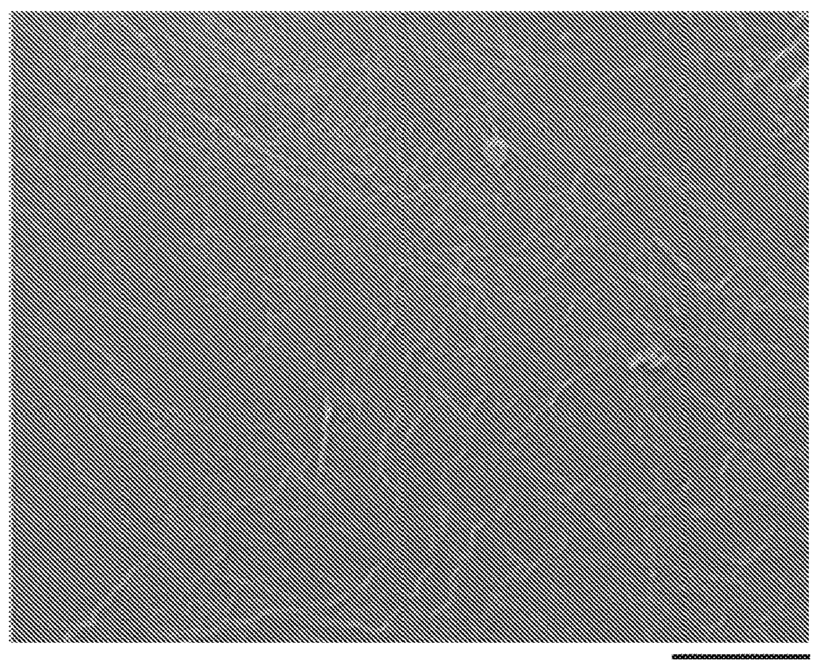
FIG. 3 is a SEM (Scanning Electron Micrograph) of the surface of coated tubing of this disclosure.
Figure 4:
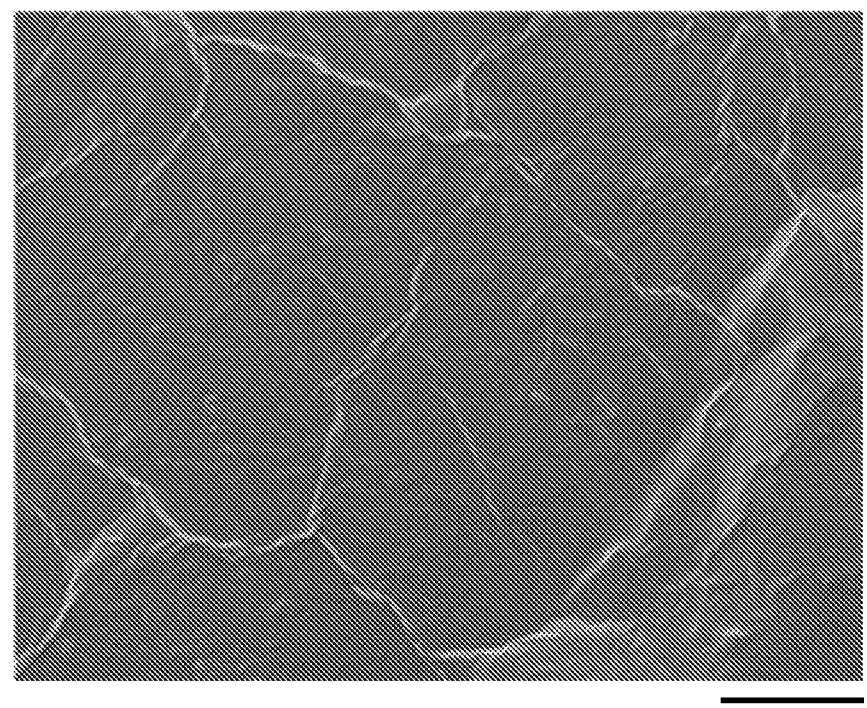
FIG. 4 is a SEM (Scanning Electron Micrograph) of the surface of another coated tubing of this disclosure.

The microcracks in the coating surface are visible in FIGS. 3 and 4. Again, not wishing to be bound by theory, it is believed that the microcracks are at least partially responsible for the flexibility of the vapor-deposited coating. Because the tubing is flexible and undergoes bending, the microcracks are believed to provide a mechanism for the vapor-deposited coating to also bend and flex and not shatter when the tubing is bent or twisted. In this way, the coating remains largely intact and is also flexible.

The anti-microbial activity of the articles of this disclosure can be modeled in a variety of ways. Particularly suitable is the comparison of the anti-microbial activity of a tube with an anti-microbial layer with or without the barrier coting. The anti-microbial activity of the anti-microbial layer even when covered with the barrier coating was surprising. The methods for carrying out this modeling are described in the Examples section.

Also disclosed are methods for preparing medical articles. In some embodiments, the method comprises providing a tube with an interior surface and an exterior surface, disposing an anti-microbial on at least a portion of the exterior surface of the tube, and vapor coating a barrier polymer derived from at least one ethylenically unsaturated monomer onto at least a portion of the exterior surface of the tube. The barrier polymer may be coated on the entire exterior surface of the tube and may also be coated on the interior surface of the tube, as has been described above. The polymeric tubing has been described above and comprises a polymer composition containing one or more extractable components.

As mentioned above, a wide range of methods of disposing an anti-microbial on at least a portion of the exterior surface of the tube may be employed. Typically, disposing an anti-microbial on at least a portion of the exterior surface of the tube comprises soaking, dipping, wiping, coating, printing, or spraying. In some embodiments, disposing an anti-microbial on at least a portion of the exterior surface of the tube comprises soaking the tube in a solution of an anti-microbial in a solvent, as described above.

A wide range of anti-microbials are suitable. In some embodiments, the anti-microbial comprises benzalkonium chloride, copper, silver, quaternary ammonium compounds, polyhexamethylene biguanide, chlorhexidine gluconate, fatty acid monoesters. Benzalkonium chloride is a particularly suitable anti-microbial.

In some embodiments, vapor coating a barrier polymer onto at least a portion of the exterior surface of the tube comprises placing the tube in a deposition chamber, applying a vacuum to the deposition chamber, heating a precursor material to volatize and optionally pyrrolyze at least a portion of it, and introducing the volatilized and optionally pyrrolyzed precursor material into the deposition chamber. The precursor material comprises the at least one ethylenically unsaturated monomer. Typically, the precursor material comprises parylene or a mixture of parylene and at least one (meth)acrylate. Suitable parylene compositions are described above. As was described above, the volatilized precursor material deposits on the tubing and polymerizes to form the barrier coating on the tubing surface. At least a portion of the exterior surface of the tubing is coated, and in many embodiments, the entire exterior surface of the tubing is coated. In some embodiments, both the interior and exterior surface of the tubing is coated. Typically, the vapor-deposited coating is optically transparent.

There are a variety of methods for placing the tubing in the deposition chamber. In some embodiments, the tubing may be placed on a rotating basket or it may be hung from a rack in the deposition chamber.

The tubing suitable for use in the methods of this disclosure are polymeric compositions with extractable components. Examples of suitable polymeric compositions have been described above. In some embodiments, the polymer compositions comprise plasticized polyvinyl chloride (PVC), plasticized PVC copolymers, plasticized polyurethane, or polysiloxanes. Polysiloxanes may or may not include plasticizers like the other classes of polymers, but even if plasticizers are not used in the polysiloxanes, they may contain a variety of extractable materials such as unreacted cyclic siloxane, catalyst residue, tackifier, plasticizer, or a combination thereof. Additionally, any of the above polymer compositions may contain additional materials that may be extractable including stabilizing agents such as thermal stabilizers and UV stabilizers, fillers, and the like.

The polymeric tubes of this disclosure may have a wide range of diameters and thicknesses. Typically, the tubes are not wide tubes, often having an internal diameter of from 1 to 10 millimeters. In some embodiments, the tube has a thickness of from 0.1-7 millimeters. The tube may have a variety of lengths, typically at least 20 centimeters, often at least 40 centimeters.

The vapor-deposited crosslinked polymer coatings have been described above. Typically, the polymer coating has a thickness of from 0.2-10 micrometers. In some embodiments, the polymer coating has a thickness of from 1-5 micrometers.

As mentioned above, the coated tubing can be used to prepare a wide variety of medical articles. In some embodiments, the coated tubes are used in stethoscopes, as has been described above.

The tubes of this disclosure also have a vapor-deposited coating of a barrier polymer derived from at least one ethylenically unsaturated monomer covering at least a portion of the exterior surface of the tube. For example, stethoscope tubing is desirably coated at least along the part of the tubing which would contact the skin when worn around the neck. In many embodiments, the entire exterior surface of the tube has a vapor-deposited coating of a barrier polymer. In some embodiments, the tube also has a vapor-deposited coating of a barrier polymer on the interior surface of the tube.

EXAMPLES

These examples are merely for illustrative purposes only and are not meant to be limiting on the scope of the appended claims. All parts, percentages, ratios, etc. in the examples and the rest of the specification are by weight, unless noted otherwise. The following abbreviations are used: cm=centimeters; g=grams; mL=milliliter; L=liter; rpm=revolutions per minute; h=hours.

Table of Abbreviations

| Abbreviation or Trade Designation | Description |
|---|---|
| BZK | benzalkonium chloride |
| PVC | Polyvinyl chloride tubes or pucks containing PolyOne phthalate-free plasticizer |
| PET | Polyethylene terephthalate |

Sample Preparation

Examples E1 and E2 and Comparative Examples CE1-CE5

Comparative Examples CE1 and CE2: PVC Coated with Parylene-C or Parylene-N

Samples of tubes and flat pucks of PVC were coated using a vacuum process statically hanging them from a rotating carousel. The samples were wiped once with isopropanol and loaded onto the carousel and placed into a parylene-coating reactor. The tubes were coated using a vacuum process at approximately 160 milliTorr. Coatings of 2.1 micrometer thickness of either Parylene-C(CE1) or Parylene-N(CE2) were prepared. On the tubing samples, the coating process coated both interior and exterior surfaces of the tubing.

Prior to parylene coating, the PVC tubes had a glossy finish and slightly tacky feel with a relatively high coefficient of friction. After application of the Parylene-C or Parylene N coating, the Parylene-coated tubes had a dry, slippery feel and a lower coefficient of friction. Parylene-N films give the tubing a very uniformly matte finish. Parylene-C films remained glossy in appearance but with a fine elephant skin finish. Tubing flexibility was not changed with either coating. The strong adhesion of the Parylene coatings were confirmed by cutting a cross hatch pattern in the coating, adhering and removing a tape sample (3M Double Sided Tape) to determine if the coating was removed, similar to the "ASTM D3359 Cross Hatch Test" test method. The Parylene coatings were not removed upon removal of the tape.

Comparative Example CE3 PVC Samples Coated by Anti-Microbial

A solution of 5% BZK was prepared in acetone. One inch (2.54 cm) diameter circular PVC pucks were placed in a tube containing 20 mL of the BZK solution and the tube was set to shake for 5 minutes. After the 5 minute period, sample was pulled out of the tube and air dried.

Comparative Example CE4 PVC Samples Soaked with Acetone

One inch (2.54 cm) diameter circular PVC pucks were placed in a tube containing 20 mL of acetone without an anti-microbial and the tube was set to shake for 5 minutes. After the 5 minute period, sample was pulled out of the tube and air dried.

Comparative Example CE5 PET Control Sample

A sample of PET without an anti-microbial coating was tested as a control sample for anti-microbial activity.

Examples E1 and E2 PVC Samples Coated with Anti-Microbial and then Coated with Parylene-C or Parylene-N A solution of 5% BZK was prepared in acetone. One inch (2.54 cm) diameter circular PVC pucks were placed in a tube containing 20 mL of the BZK solution and the tube was set to shake for 5 minutes. After the 5 minute period, samples were pulled out of the tube and air dried. Samples were then coated in Parylene C (Example E1) or Parylene N (Example E2) as described above for Comparative Examples CE1 and CE2. Scanning electron micrographs (SEM) of a Parylene coated sample for Example E1 (Parylene-C) are shown in FIG. 3 and the parylene coated sample for Example E2 (Parylene-N) are shown in FIG. 4. FIGS. 3 and 4 show the microcracking present in the Parylene coatings.

Anti-Microbial Testing

Sample Preparation

JIS Z2801 Method: Antimicrobial Products-Test for Antimicrobial Activity and Efficacy Media Preparation: Tryptic soy broth (TSB) was prepared as directed on the manufacturer's label by dissolving 37 g/L in deionized water and filter sterilizing the solution.

Bacterial Culture: Tryptic Soy Agar was prepared per the manufacturer's instructions on the bottle. A streak plate of *Staphylococcus aureus* (ATCC 6538) was prepared from a frozen stock on Tryptic Soy Agar and left at 37° C. overnight to incubate. An overnight culture of *Staphylococcus aureus* (ATCC 6548) or *Pseudomonas aeruginosa* (ATCC 15442) was grown by selecting a single colony and inoculating a tube with 10 mL of TSB then incubated at 37° C. while shaking at 250 rpm for 12-16 hours. Two 1-mL aliquots of the overnight culture were centrifuged at 5000×g for 5 minutes to pellet the cells, the supernatant was removed from each and the bacteria in each tube were resuspended in 1 mL of phosphate buffered saline (PBS; pH 7.4). The 1 mL of PBS containing *S. aureus* or *P. aeruginosa* from one tube was then transferred to a 15-mL conical vial and diluted with PBS to a final volume of 10 mL. The resulting solution was used as the PBS inoculum.

Sample Inoculation and Incubation: Samples were inoculated by pipetting 100 microliters of the corresponding inoculation solution (in PBS) onto one of the PVC pucks in each well. The second puck in each well was then placed on top of the inoculum on the first disc, sandwiching the inoculum between the two film samples. After inoculation, half of the 6-well plates were placed inside a Ziploc bag containing a paper towel saturated with water and moved to 37° C. for a 24 h static incubation. The other half of the samples were harvested immediately for quantitative recovery at the 0 h time point. All samples were prepared in triplicate.

Sample recovery: Each sample was transferred to an individual 50-mL conical vial containing 10 mL of PBS buffer containing 0.05% Tween 20. Each tube was vortexed for 1 minute, then sonicated for 1 minute using a Branson Ultrasonic Cleaner, then vortexed for 1 minute. After the second vortexing step, each tube was serially diluted in Butterfield's buffer to the −8 dilution (the original tube served as the −1 dilution) and 1 mL from each dilution was plated on 3M AEROBIC COUNT PetriFilm. The PetriFilm was incubated at 37° C. for 24 hours. The number of colony forming units (CFU) on each plate were counted after the 24 hour incubation using a 3M PetriFilm reader.

Results

The log reduction data generated using the test method JIS A2801 are shown in Table 1 below. The log reduction data shows the efficacy of the BZK underneath the Parylene coatings (9.41 log reduction of *Pseudomonas aeruginosa* ATCC PA15442). Additionally, there is no decrease in antimicrobial efficacy at the 24 hour time point between the BZK on the PVC surface and the BZK covered by the Parylene coating.

TABLE 1

| Sample | Average CFU (24 h)* | Log10 Average | Log 10 Reduction |
|---|---|---|---|
| CE1 | $6.77 \times 10^8$ | 8.83 | 0.58 |
| CE2 | $6.17 \times 10^8$ | 8.79 | 0.62 |
| E1 | 0.00 | 0.00 | 9.41 |
| E2 | 0.00 | 0.00 | 9.41 |
| CE3 | 0.00 | 0.00 | 9.41 |
| CE4 | $3.11 \times 10^8$ | 8.49 | 0.92 |
| CE5 | $4.93 \times 10^8$ | 8.69 | 0.72 |

*0 hour Inoculation Control = 9.41 logs

What is claimed is:

1. A medical article comprising:

a tube with an interior surface and an exterior surface, comprising a polymer composition containing one or more extractable components, and wherein at least a portion of the exterior surface of the tube contains an anti-microbial; and a transparent vapor-deposited coating of a barrier polymer derived from at least one ethylenically unsaturated monomer covering at least a portion of at least the exterior surface of the tube, such that the vapor-deposited coating reduces the extraction of extractable component(s) from the tube, and wherein the vapor-deposited coating has at least one crack, and wherein the anti-microbial is capable of passing through or being exposed by the at least one crack of the vapor-deposited coating so as to provide anti-microbial activity.

2. The medical article of claim 1, wherein the polymer composition containing one or more extractable components comprises:

plasticized polyvinyl chloride (PVC);

plasticized PVC copolymers;

plasticized polyurethane; or polysiloxane containing unreacted cyclic siloxane, catalyst residue, plasticizer, tackifier, or a combination thereof.

3. The medical article of claim 1, wherein the anti-microbial comprises benzalkonium chloride, copper, silver, quaternary ammonium compounds, polyhexamethylene biguanide, chlorhexidine gluconate, or fatty acid monoesters.

4. The medical article of claim 1, wherein the vapor-deposited coating covers at least a portion of the interior surface of the tube.

5. The medical article of claim 1, further comprising a discontinuous or continuous layer on the exterior surface of the tube, wherein the discontinuous or continuous layer comprises a graphic layer.

6. The medical article of claim 1, wherein the vapor-deposited coating comprises parylene.

7. The medical article of claim 6, wherein parylene comprises parylene N, parylene C, parylene D, or parylene HT.

8. The medical article of claim 1, wherein the vapor-deposited coating has a thickness of from 0.2-10 micrometers.

9. The medical article of claim 1, wherein the vapor-deposited coating has a thickness of from 1-5 micrometers.

10. The medical article of claim 1, wherein the polymer composition containing one or more extractable components has a thickness of from 0.1-7 millimeters.

11. The medical article of claim 1, wherein the tube comprises tubing for a stethoscope.

12. The medical article of claim 1, wherein the vapor-deposited coating comprises a copolymer of parylene and at least one (meth)acrylate.

13. The medical article of claim 12, wherein the at least one (meth)acrylate comprises at least one $C_3$-$C_{18}$ alkyl (meth)acrylate.

14. A method of preparing a medical article comprising:
providing a tube with an interior surface and an exterior surface, comprising a polymer composition containing one or more extractable components;
disposing an anti-microbial on at least a portion of the exterior surface of the tube; and
vapor coating a barrier polymer derived from at least one ethylenically unsaturated monomer onto at least a portion of at least the exterior surface of the tube to form a vapor-deposited coating that has at least one crack, and wherein the anti-microbial is capable of passing through or being exposed by the at least one crack of the vapor-deposited coating so as to provide anti-microbial activity.

15. The method of claim 14, wherein disposing an anti-microbial on at least a portion of the exterior surface of the tube comprises soaking, dipping, wiping, coating, printing, or spraying.

16. The method of claim 15, wherein disposing an anti-microbial on at least a portion of the exterior surface of the tube comprises soaking the tube in a solution of an anti-microbial in a solvent.

17. The method of claim 14, wherein the anti-microbial comprises benzalkonium chloride, copper, silver, quaternary ammonium compounds, polyhexamethylene biguanide, chlorhexidine gluconate, fatty acid monoesters.

18. The method of claim 14, wherein vapor coating a barrier polymer onto at least a portion of at least the exterior surface of the tube comprises:
placing the tube in a deposition chamber;
applying a vacuum to the deposition chamber;
heating a precursor material to volatize at least a portion of it; and
introducing the volatilized precursor material into the deposition chamber, wherein the precursor material comprises parylene or a mixture of parylene
and at least one (meth)acrylate.

19. The method of claim 14, wherein the vapor coating of the barrier polymer has a thickness of from 0.2-10 micrometers.

20. The method of claim 14, wherein the tube comprises tubing for a stethoscope.

* * * * *